United States Patent

Hübscher et al.

Patent Number: 6,153,549
Date of Patent: Nov. 28, 2000

[54] METALLOCENES

[75] Inventors: Erich Hübscher, Kelkheim; Roland Zenk, Bad Soden, both of Germany

[73] Assignee: Targor GmbH, Ludwigshafen, Germany

[21] Appl. No.: 08/962,383

[22] Filed: Oct. 31, 1997

[30] Foreign Application Priority Data

Oct. 31, 1996 [DE] Germany .............................. 196 44 039

[51] Int. Cl.⁷ .............................. B01J 31/00; C07F 17/00; C08F 4/02

[52] U.S. Cl. ................................ 502/103; 556/9; 556/12; 556/43; 556/53; 556/58; 526/129; 526/160; 526/943; 502/117; 502/152

[58] Field of Search .................................. 556/9, 12, 43, 556/53, 58; 502/103, 117, 152; 526/129, 160, 943

[56] References Cited

U.S. PATENT DOCUMENTS

| | | | |
|---|---|---|---|
| 5,017,714 | 5/1991 | Welborn et al. | 556/12 |
| 5,120,867 | 6/1992 | Welborn, Jr. | 556/12 |
| 5,268,495 | 12/1993 | Riepl et al. | 556/11 |
| 5,276,208 | 1/1994 | Winter et al. | 556/53 |

FOREIGN PATENT DOCUMENTS

| | | |
|---|---|---|
| 0 490 887 | 12/1989 | European Pat. Off. |
| 0 490 256 | 6/1992 | European Pat. Off. |
| 0 611 773 | 8/1994 | European Pat. Off. |
| WO 95 27717 | 10/1995 | WIPO |

*Primary Examiner*—Porfirio Nazario-Gonzalez
*Attorney, Agent, or Firm*—Connolly Bove Lodge & Hutz LLP

[57] ABSTRACT

The present invention relates to a new metallocene having the formula (I)

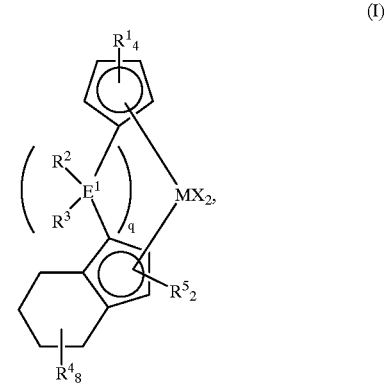

where
M is a metal of group IVb, Vb or VIb of the Periodic Table of the Elements, in particular Ti, Zr and Hf, X are identical or different and are each a hydrogen atom, a $C_1$–$C_{40}$-hydrocarbon group such as a $C_1$–$C_{10}$-alkyl, $C_1$–$C_{10}$-alkoxy, $C_6$–$C_{10}$-aryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl group, an OH group, a halogen atom or a pseudohalogen such as nitrile, $R^1$ to $R^5$ are identical or different and, independently of one another, are each a hydrogen atom, a $C_1$–$C_{30}$-hydrocarbon radical such as $C_1$–$C_{20}$-alkyl or $C_6$–$C_{20}$-aryl, or a carbon-containing radical having from 1 to 10 carbon atoms and one or more heteroatoms selected from the group consisting of O, N, Si, Ge and P, where in each case two adjacent radicals $R^4$ and/or $R^1$ together with the carbon atoms connecting them can form a ring system, $E^1$ is a carbon, silicon, germanium or tin atom, preferably a carbon atom, and q is 0 or 1, preferably 1.

18 Claims, No Drawings

METALLOCENES

The present invention relates to hydrogenated and partially hydrogenated metallocenes.

Hydrogenated metallocenes such as ethylenebis(tetrahydroindenyl)zirconium dichloride and dimethylsilanediylbis(tetrahydroindenyl)zirconium dichloride are known from J. Am. Chem. Soc. (1996), 118, 2105, J. Mol. Catal. A. Chem. (1995), 102, 59, EP-A-0 643 079, Macromolecules (1994), 27, 4477, Macromolecules (1996), 29, 2331 and JP-A-07 292 019. They are suitable for preparing polyolefins such as isotactic polypropylene, copolymers and elastomers, in addition, a series of further hydrogenated metallocenes are known, cf. EP-A-0 581 754, EP-A-529 908, Organometallics (1993), 12, 4391, JP-A-07 041 521 and Chem. Ber. (1994), 127, 2417. Hydrogenated and partially hydrogenated metallocenes are described as catalyst precursors for the polymerization of olefins, cf. J. Organomet. Chem. (1995), 497, 181, Angew. Chem. (1992), 104, 1373, EP-A-0 344 887, J. Mol. Catal. A. Chem. (1995), 102, 59, EP-A-0 185 918, EP-A-0 537 686 and EP-A-485 821.

The synthesis of hydrogenated or partially hydrogenated metallocenes generally starts from the corresponding hydrogenable metallocenes containing aromatic ligands. Thus, hydrogenation of dimethylsilanediylbisindenylzirconium dichloride gives the octahydro derivative dimethylsilanediylbis(4,5,6,7-tetrahydroindenyl)zirconium dichloride. Such and similar reactions have been described many times, cf. JP-A-06 287 224, EP-A-344 887, J. Organomet. Chem. (1995), 497,181, Organometallics (1991), 10, 1501 and J. Organomet. Chem. (1988), 342, 21.

The known synthetic procedures for the hydrogenation of the aromatic ligand skeleton of metallocenes in principle all follow the same route. The nonhydrogenated metallocene is dissolved or suspended in dichloromethane and hydrogenated under a high hydrogen pressure in the presence of platinum black or platinum dioxide, cf. J. Organomet. Chem. (1988), 342, 21 and EP-A-344 887.

Dichloromethane and other chlorinated solvents can be used in relatively large amounts only if strict safety and environmental regulations are adhered to. In chlorinated solvents, only weakly activating hydrogenation catalysts such as platinum black or platinum dioxide can be used in order to avoid dehalogenation reactions. The dehalogenation reactions lead to the decomposition of the product and to corrosion problems.

It is an object of the invention to provide new hydrogenated and partially hydrogenated metallocenes.

This object is achieved by metallocenes having the formula (I).

The present invention accordingly provides metallocenes of the formula (I)

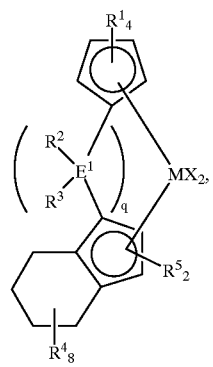

(I)

where
- M is a metal of group IVb, Vb or VIb of the Periodic Table of the Elements, in particular Ti, Zr and Hf,
- X are identical or different and are each a hydrogen atom, a $C_1$–$C_{40}$-hydrocarbon group such as a $C_1$–$C_{10}$-alkyl, $C_1$–$C_{10}$-alkoxy, $C_6$–$C_{10}$-aryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl group, an OH group, a halogen atom or a pseudohalogen such as nitrile,
- $R^1$ to $R^5$ are identical or different and, independently of one another, are each a hydrogen atom, a $C_1$–$C_{30}$-hydrocarbon radical such as $C_1$–$C_{20}$-alkyl or $C_6$–$C_{20}$-aryl, or a carbon-containing radical having from 1 to 10 carbon atoms and one or more heteroatoms selected from the group consisting of O, N, Si, Ge and P, where in each case two adjacent radicals $R^4$ and/or $R^1$ together with the carbon atoms connecting them can form a ring system,
- $E^1$ is a carbon, silicon, germanium or tin atom, preferably a carbon atom, and
- q is 0 or 1, preferably 1.

Preference is given to metallocenes in which
- M is zirconium or hafnium,
- X is a $C_1$–$C_4$-alkyl, $C_1$–$C_3$-alkoxy, $C_6$–$C_8$-aryl, $C_6$–$C_8$-aryloxy, $C_2$–$C_4$-alkenyl, $C_7$–$C_{12}$-arylalkyl, $C_7$–$C_{12}$-alkylaryl or $C_8$–$C_{12}$-arylalkenyl group or chlorine,
- $E^1$ is a carbon atom,
- $R^2$ and $R^3$ are $C_1$–$C_4$-alkyl such as methyl, ethyl or $C_6$–$C_{14}$-aryl such as phenyl,
- q is 0 or 1, preferably 1.

Examples of metallocenes according to the invention are listed below, but this list is not limiting:
(cyclopentadienyl)(4,5,6,7-tetrahydroindenyl)zirconium dichloride,
(methylcyclopentadienyl)(2-methyl-4,5,6,7-tetrahydroindenyl)zirconium dichloride,
bis(2-methyl-4,5-benzo-6,7-dihydroindenyl)zirconium dichloride,
bis(4,5,6,7-tetrahydroindenyl)zirconium dichloride,
bis(2-methyl4,5,6,7-tetrahydroindenyl)zirconium dichloride, bis(2-methyl-4,5,6,7-tetrahydroindenyl)hafnium dichloride,
isopropylidene(cyclopentadienyl)(4,5,6,7-tetrahydroindenyl)zirconium dichloride,
isopropylidene(cyclopentadienyl)(4,5,6,7-tetrahydroindenyl)hafnium dibromide,
rac-isopropylidenebis(4,5,6,7-tetrahydroindenyl)zirconium dichloride,
meso-isopropylidenebis(4,5,6,7-tetrahydroindenyl)zirconium dichloride,
meso-dimethylsilanediylbis(4,5,6,7-tetrahydroindenyl)zirconium dichloride,
rac-dimethylsilanediylbis(2-methyl-4,5,6,7-tetrahydroindenyl)zirconium dibromide,
meso-dimethylsilanediylbis(2-methyl-4,5,6,7-tetrahydroindenyl)zirconium dichloride,
rac-dimethylsilanediylbis(2-methyl-4-phenyl-4,5,6,7-tetrahydroindenyl)zirconium dichloride,
meso-dimethylsilanediylbis(2-methyl-4-phenyl-4,5,6,7-tetrahydroindenyl)zirconium dichloride,
rac-dimethylsilanediylbis[2-methyl-4-(1-naphthyl)-4,5,6,7-tetrahydroindenyl]zirconium dichloride,
rac-dimethylsilanediylbis[2-methyl-4-(1-naphthyl)-4,5,6,7-tetrahydroindenyl]hafnium dichloride,
meso-dimethylsilanediylbis[2-methyl-4-(1-naphthyl)-4,5,6,7-tetrahydroindenyl]zirconium dichloride,
rac-dimethylsilanediylbis(2-methyl-4,5,6,7-tetrahydro-4,5-benzoindenyl)zirconium dichloride,
meso-dimethylsilanediylbis(2-methyl-4,5,6,7-tetrahydro-4,5-benzoindenyl)zirconium dichloride,
rac-dimethylsilanediylbis(4,5,6,7-tetrahydro-4,5-benzoindenyl)zirconium dichloride,
meso-dimethylsilanediylbis(4,5,6,7-tetrahydro-4,5-benzoindenyl)zirconium dichloride,
rac-dimethylsilanediylbis(2-methyl-4,6-diisopropyl-indenyl)zirconium dichloride,
rac-dimethylsilanediylbis(2-methyl-4,6-diisopropyl-4,5,6,7-tetrahydroindenyl)zirconium difluoride,
meso-dimethylsilanediylbis(2-methyl-4,6-diisopropyl-4,5,6,7-tetrahydroindenyl)zirconium dichloride,
rac-dimethylsilanediylbis(2-ethyl-4,5,6,7-tetrahydroindenyl)zirconium dichloride,
meso-dimethylsilanediylbis(2-ethyl-4,5,6,7-tetrahydroindenyl)zirconium dichloride,
rac-dimethylsilanediylbis(2-ethyl-4-phenyl-4,5,6,7-tetrahydroindenyl)zirconium dichloride,
rac-dimethylsilanediylbis(2-ethyl-4-phenyl-4,5,6,7-tetrahydroindenyl)hafnium dichloride,
meso-dimethylsilanediylbis(2-ethyl-4-phenyl-4,5,6,7-tetrahydroindenyl)zirconium dichloride,
rac-dimethylsilanediylbis[2-ethyl-4-(1-naphthyl)-4,5,6,7-tetrahydroindenyl]-zirconium dichloride,
meso-dimethylsilanediylbis[2-ethyl-4-(1-naphthyl)-4,5,6,7-tetrahydroindenyl]zirconium dichloride,
rac-dimethylsilanediylbis(2-ethyl-4,5,6,7-tetrahydro-4,5-benzoindenyl)zirconium dichloride,
meso-dimethylsilanediylbis(2-ethyl-4,5,6,7-tetrahydro-4,5-benzoindenyl)zirconium dichloride,
rac-dimethylsilanediylbis(4,5-benzo-4,5,6,7-tetrahydroindenyl)zirconium dichloride,
meso-dimethylsilanediylbis(4,5,6,7-tetrahydro-4,5-benzoindenyl )zirconium dichloride,
rac-dimethylsilanediylbis(2-ethyl-4,6-diisopropyl-4,5,6,7-tetrahydroindenyl)-zirconium dichloride,
meso-dimethylsilanediylbis(2-ethyl-4,6-diisopropyl4,5,6,7-tetrahydroindenyl)zirconium dichloride,
rac-dimethylsilanediylbis(2-ethyl-4,6-dimethyl-4,5,6,7-tetrahydroindenyl)zirconium dichloride,
meso-dimethylsilanediylbis(2-ethyl-4,6-dimethyl-4,5,6,7-tetrahydroindenyl)-zirconium dichloride,
rac-dimethylsilanediylbis(2,4,6-trimethylindenyl)zirconium dichloride,
rac-dimethylsilanediylbis(2,4,6trimethyl-4,5,6,7-tetrahydroindenyl)hafnium dichloride,
meso-dimethylsilanediylbis(2,4,6-trimethyl-4,5,6,7-tetrahydroindenyl)zirconium dichloride.

Preference is given to:
isopropylidene(cyclopentadienyl)(4,5,6,7-tetrahydroindenyl)zirconium dichloride,
diphenylmethylene(cyclopentadienyl)(4,5,6,7-tetrahydroindenyl)zirconium dichloride,
methylphenylmethylene(cyclopentadienyl)(4,5,6,7-tetrahydroindenyl)zirconium dichloride,
isopropylidene(cyclopentadienyl)(4,5,6,7-tetrahydroindenyl)hafnium dichloride,
diphenylmethylene(cyclopentadienyl)(4,5,6,7-tetrahydroindenyl)hafnium dichloride,
methylphenylmethylene(cyclopentadienyl)(4,5,6,7-tetrahydroindenyl)hafnium dichloride,
isopropylidenebis(4,5,6,7-tetrahydroindenyl)zirconium dichloride,
diphenylmethylenebis(4,5,6,7-tetrahydroindenyl)zirconium dichloride,
methylphenylmethylenebis(4,5,6,7-tetrahydroindenyl)zirconium dichloride,
isopropylidenebis(4,5,6,7-tetrahydroindenyl)hafnium dichloride,
diphenylmethylenebis(4,5,6,7-tetrahydroindenyl)hafnium dichloride and
methylphenylmethylenebis(4,5,6,7-tetrahydroindenyl)hafnium dichloride.

The novel metallocenes of the formula I are prepared by hydrogenation of hydrogenable metallocenes, where at least one metallocene containing at least one hydrogenable double bond (hereinafter: the nonhydrogenated metallocene) in at least one nonhalogenated solvent is treated with hydrogen in the presence of at least one hydrogenation catalyst.

Nonhydrogenated metallocenes are described, for example, in EP-A-344 882, EP-A-485 823, EP-A416 566 or EP-A-610 851.

Nonhydrogenated metallocenes such as dimethylsilanediylbisindenylzirconium dichloride or ethylenebisindenylzirconium dichloride are preferably hydrogenated in nonhalogenated aromatic solvents and/or in nonhalogenated oxygen-containing aprotic solvents. Mixtures of the solvents mentioned can also be used.

The term nonhydrogenated metallocene refers to the metallocene from which the novel partially hydrogenated or hydrogenated metallocene of the formula (I) is prepared.

The hydrogenation product is a metallocene which has an altered structure and altered polymerization properties and differs from the nonhydrogenated metallocene used in that at least one of the double bonds present in the nonhydrogenated metallocene used is hydrogenated.

Examples of nonhydrogenated metallocenes are listed below, but this list is nonlimiting:
(cyclopentadienyl)(indenyl)zirconium dichloride,
(methylcyclopentadienyl)(2-methylindenyl)zirconium dichloride,
bisindenylzirconium dichloride,
bisindenylhafnium dichloride,
bis(2-methyl-4,5-benzoindenyl)zirconium dichloride,
bis(2-methylindenyl)zirconium dichloride,
bis(2-methylindenyl)hafnium dichloride,
isopropylidene(cyclopentadienyl)(indenyl)zirconium dichloride, isopropylidene(cyclopentadienyl)(indenyl)hafnium dibromide,
rac-isopropylidenebisindenylzirconium dichloride,
meso-isopropylidenebisindenylzirconium dichloride,
rac-dimethylsilanediylbisindenylzirconium dichloride,
meso-dimethylsilanediylbisindenylzirconium dichloride,
rac-dimethylsilanediylbis(2-methylindenyl)zirconium dibromide,
meso-dimethylsilanediylbis(2-methylindenyl)zirconium dichloride,
rac-dimethylsilanediylbis(2-methyl-4-phenylindenyl)zirconium dichloride,
meso-dimethylsilanediylbis(2-methyl-4-phenylindenyl)zirconium dichloride,
rac-dimethylsilanediylbis[2-methyl-4-(1-naphthyl)indenyl]zirconium difluoride,
rac-dimethylsilanediylbis[2-methyl-4-(1-naphthyl)indenyl]hafnium dichloride,
meso-dimethylsilanediylbis[2-methyl-4-(1-naphthyl)indenyl]zirconium dichloride,
rac-dimethylsilanediylbis(2-methyl-4,5-benzoindenyl)zirconium dichloride,
meso-dimethylsilanediylbis(2-methyl-4,5-benzoindenyl)zirconium dichloride,
rac-dimethylsilanediylbis(4,5-benzoindenyl)zirconium dichloride,
meso-dimethylsilanediylbis(4,5-benzoindenyl)zirconium dichloride,
rac-dimethylsilanediylbis(2-methyl-4,6-diisopropylindenyl)zirconium difluoride,
meso-dimethylsilanediylbis(2-methyl-4,6-diisopropylindenyl)zirconium dichloride,
rac-dimethylsilanediylbis(2-ethylindenyl)zirconium dichloride,
meso-dimethylsilanediylbis(2-ethylindenyl)zirconium dichloride,
rac-dimethylsilanediylbis(2-ethyl-4-phenylindenyl)zirconium dichloride,
rac-dimethylsilanediylbis(2-ethyl-4-phenylindenyl)hafnium dichloride,
reso-dimethylsilanediylbis(2-ethyl-4- phenylindenyl)zirconium dichloride,
rac-dimethylsilanediylbis[2-ethyl-4-(1-naphthyl)indenyl]zirconium dichloride,
meso-dimethylsilanediylbis[2-ethyl-4-(1-naphthyl)indenyl]zirconium dichloride,
rac-dimethylsilanediylbis(2-ethyl-4,5-benzoindenyl)zirconium dichloride,
meso-dimethylsilanediylbis(2-ethyl-4,5-benzoindenyl)zirconium dichloride,
rac-dimethylsilanediylbis(4,5-benzoindenyl)zirconium dichloride,
meso-dimethylsilanediylbis(4,5-benzoindenyl) zirconium dichloride,
rac-dimethylsilanediylbis(2-ethyl-4,6-diisopropylindenyl)zirconium dichloride,
meso-dimethylsilanediylbis(2-ethyl-4,6-diisopropylindenyl)zirconium dichloride,
rac-dimethylsilanediylbis(2-ethyl-4,6-dimethylindenyl)zirconium dichloride,
meso-dimethylsilanediylbis(2-ethyl-4,6-dimethylindenyl)zirconium dichloride,
rac-dimethylsilanediylbis(2,4,6-trimethylindenyl)zirconium dichloride,
rac-dimethylsilanediylbis(2,4,6-trimethylindenyl)hafnium dichloride,
meso-dimethylsilanediylbis(2,4,6-trimethylindenyl)zirconium dichloride.

Apart from the nonhydrogenated metallocene, the starting materials can comprise, as further constituents, inorganic salts such as NaCl, LiCl, KCl, KBr, $MgCl_2$, $MgBr_2$, MgBrCl, $CaCl_2$, $AlCl_3$ or filter aids such as $Na_2SO_4$, quartz flour or Celite. Further constituents can also be organic and organometallic secondary components. Organic secondary components are solvent residues, organic impurities from the starting materials, unreacted starting materials and incompletely reacted intermediates of the metallocene synthesis. Organometallic secondary components can be isomeric metallocenes, oligomeric metallocenes and compounds which have been formed in the preparation of the raw material or have been introduced as a result of impurities in the starting compounds. Organometallic secondary components are all compounds which have at least one metal-carbon bond with the exception of the nonhydrogenated metallocene itself.

Aromatic solvents are solvents which have at least one aromatic 6-membered ring per molecule. Examples of non-halogenated aromatic solvents are benzene, toluene, xylene (as an isomer mixture), o-xylene, m-xylene, p-xylene, mesitylene, tetralin, anisole, cumene, 1,2-diethylbenzene, 1,3-diethylbenzene, 1,4-diethylbenzene, 1-ethyl-2-methylbenzene, 1-ethyl-3-methylbenzene, 1-ethyl-4-methyl benzene. Preference is given to anisole, toluene, benzene, xylenes (as a mixture or pure substance) and tetralin.

The nonhalogenated oxygen-containing aprotic solvents include aromatic and aliphatic ethers such as anisole, ethyl phenyl ether, isopropyl phenyl ether, diethyl ether, di-n-butyl ether, tert-butyl methyl ether, tetrahydrofuran, dioxane. In addition, it is also possible to use esters of aliphatic or aromatic carboxylic acids as solvents, for example ethyl acetate and propyl butyrate.

The preparative process is carried out in a temperature range of preferably from 0° C. to 50° C. In particular, the hydrogenation is carried out at from 15° C. to 100° C.

Suitable hydrogenation catalysts are compounds or elements which do not hydrogenate or only partially hydrogenate the solvent under the hydrogenation conditions employed. Examples of such hydrogenation catalysts are palladium on activated carbon, palladium on barium sulfate, palladium on aluminum oxide, palladium black, palladium sponge, platinum oxide, platinum black, platinum sponge. Preference is given to palladium catalysts, in particular palladium on activated carbon.

Surprisingly, the process has many advantages. Use of nonhalogenated (e.g. nonchlorinated) solvents makes it possible to use more active hydrogenation catalysts and the reactions can be carried out at relatively low hydrogen pressures. This is of particular interest for industrial applications. The halogenated (e.g. chlorinated) solvents which are dubious from safety and environmental points of view are avoided. Use of nonhalogenated aromatic hydrocarbons or nonhalogenated slightly polar aprotic solvents such as ethers makes the subsequent work-up of the metallocene easier. In the case of the preferred solvents such as anisole, toluene, benzene, xylene, tert-butyl methyl ether and tetrahydrofuran, the product can be completely dissolved at elevated temperature, the hydrogenation catalyst can be separated off and the product can be crystallized. In this work-up, a wider temperature range at temperatures above 0° C. is available compared to dichloromethane. Dichloromethane has hitherto been used exclusively in the prior art. Low temperatures (below 0° C.) can therefore be avoided in the crystallization. The good solubility of the hydrogenated products in nonhalogenated aromatic solvents at elevated temperature makes it possible to hydrogenate very concentrated metallocene suspensions, which is advantageous in terms of a good space-time yield. Furthermore, compared to known processes, the required amounts of hydrogenation catalyst are significantly cheaper. If metallocenes are extracted from their crude product mixtures using aromatic or aprotic aliphatic solvents, it may be possible to subject such extracts as solution or suspension to a subsequent hydrogenation directly and without change of solvent.

The novel metallocenes of the formula (I) are suitable for preparing a polyolefin by polymerization of at least one olefin in the presence of a catalyst comprising at least one cocatalyst and at least one metallocene. For the purposes of the present invention, the term polymerization refers to both homopolymerization and copolymerization.

The novel metallocenes of the formula (I) can be used for the polymerization of one or more olefins of the formula $R^\alpha$—CH=CH—$R^\beta$, where $R^\alpha$ and $R^\beta$ are identical or different and are each a hydrogen atom or a hydrocarbon radical having from 1 to 20 carbon atoms, in particular from 1 to 10 carbon atoms, and $R^\alpha$ and $R^\beta$ together with the atoms connecting them can form one or more rings. Examples of such olefins are 1-olefins having from 2 to 40, preferably 2–10, carbon atoms, for example ethylene, propylene, 1-butene, 1-pentene, 1-hexene, 4-methyl-1-pentene or 1-octene, styrene, dienes such as 1,3-butadiene, isoprene, 1,4-hexadiene or cyclic olefins such as norbornene or ethylidenenorbornene. Preference is given to homopolymerizing ethylene or propylene or copolymerizing ethylene with one or more cyclic olefins such as norbornene and/or one or more acyclic 1-olefins having from 3 to 20 carbon atoms, e.g. propylene, and/or one or more dienes having from 4 to 20 carbon atoms, e.g. 1,3-butadiene or 1,4-hexadiene. Examples of such copolymers are ethylene-norbornene copolymers, ethylene-propylene copolymers and ethylene-propylene-1,4-hexadiene copolymers.

The polymerization is preferably carried out at a temperature of from −60 to 250° C., particularly preferably from 50 to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. Preferred embodiments are gas-phase and solution polymerization.

The catalyst used preferably comprises one metallocene compound. It is also possible to use mixtures of two or more metallocene compounds, e.g. for preparing polyolefins having a broad or multimodal molecular weight distribution.

In principle, a suitable cocatalyst is any compound which, owing to its Lewis acidity, can convert the neutral metallocene into a cation and stabilize the latter ("labile coordination"). Furthermore, the cocatalyst or the anion formed therefrom should undergo no further reactions with the metallocene cation formed (EP 427 697). As cocatalyst, preference is given to using an aluminum compound and/or a boron compound.

The boron compound preferably has the formula $R^a_x NH_{4-x} BR^b_4$, $R^a_x PH_{4-x} BR^b_4$, $R^a_3 CBR^b_4$ or $BR^b_3$, where x is a number from 1 to 4, preferably 3, the radicals $R^a$ are identical or different, preferably identical, and are $C_1$–$C_{10}$-alkyl or $C_6$–$C_{18}$-aryl, or two radicals $R^a$ together with the atoms connecting them form a ring, and the radicals $R^b$ are identical or different, preferably identical, and are $C_6$–$C_{18}$-aryl which may be substituted by alkyl, haloalkyl or fluorine. In particular, $R^a$ is ethyl, propyl, butyl or phenyl and $R^b$ is phenyl, pentafluorophenyl, 3,5-bis(trifluoromethyl)phenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula C for the linear type and/or of the formula D for the cyclic type,

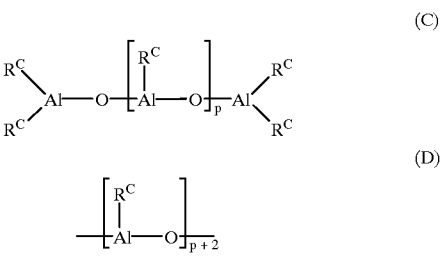

where, in the formulae C and D, the radicals $R^c$ are identical or different and are each hydrogen or a $C_1$–$C_{20}$-hydrocarbon group such as a $C_1$–$C_{18}$-alkyl group, a $C_6$–$C_{18}$-aryl group or benzyl, and p is an integer from 2 to 50, preferably from 10 to 35.

The radicals $R^c$ are preferably identical and are hydrogen, methyl, isobutyl, phenyl or benzyl, particularly preferably methyl.

If the radicals $R^c$ are different, then they are preferably methyl and hydrogen or alternatively methyl and isobutyl, where hydrogen or isobutyl is preferably present in a proportion by number of from 0.01 to 40% (of the radicals $R^c$).

The methods of preparing the aluminoxanes are known. The precise spatial structure of the aluminoxanes is not known (J. Am. Chem. Soc. (1993) 115, 4971). For example, it is conceivable that chains and rings are joined to form larger two-dimensional or three-dimensional structures.

Regardless of the method of preparation, all aluminoxane solutions have in common a varying content of unreacted aluminum starting compound which is present in free form or as adduct.

The metallocene compound can be preactivated with a cocatalyst, in particular an aluminoxane, prior to use in the polymerization reaction. This significantly increases the polymerization activity. The preactivation of the metallocene compound is preferably carried out in solution. In this preactivation step, the metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is preferably carried out at a temperature of from −78° to 100° C., preferably from 0° to 80° C.

The metallocene compound is preferably employed in a concentration, based on the transition metal, of from $10^{-3}$ to $10^{-8}$ mol, preferably from $10^{-4}$ to $10^{-7}$ mol, of transition metal per dm$^3$ of solvent or per dm$^3$ of reactor volume. The aluminoxane is preferably used in a concentration of from $10^{-6}$ to $10^{-1}$ mol, preferably from $10^{-5}$ to $10^{-2}$ mol, per dm$^3$ of solvent or per dm$^3$ of reactor volume. The other cocatalysts mentioned are used in approximately equimolar amounts to the metallocene compound. However, higher concentrations are also possible in principle.

The aluminoxane can be prepared in various ways by known methods. One of the methods is, for example, reacting an aluminum hydrocarbon compound and/or a hydridoaluminum hydrocarbon compound with water (gaseous, solid, liquid or bound—for example as water of crystallization) in an inert solvent (for example toluene). To prepare an aluminoxane having different radicals $R^c$, for example, two different trialkylaluminums corresponding to the desired composition are reacted with water.

To remove catalyst poisons present in the olefin, purification using an aluminum compound, preferably an aluminum alkyl such as trimethylaluminum or triethylaluminum is advantageous. This purification can be carried out either in the polymerization system itself or the olefin is brought into contact with the aluminum compound and subsequently separated off again before addition to the polymerization system.

As molecular weight regulator and/or for increasing the catalyst activity, hydrogen can be added in the process of the invention. This enables lower molecular weight polyolefins such as waxes to be obtained.

The metallocene compound is preferably reacted with the cocatalyst outside the polymerization reactor in a separate step using a suitable solvent. Application to a support can be carried out during this step.

In the process for preparing a polyolefin, a prepolymerization can be carried out with the aid of the metallocene compound. The prepolymerization is preferably carried out using the (or one of the) olefin(s) used in the polymerization.

The catalyst used can be supported. Application to a support enables, for example, the particle morphology of the olefin prepared to be controlled. The metallocene compound can be reacted first with the support and subsequently with the cocatalyst. The cocatalyst can also be supported first and subsequently reacted with the metallocene compound. It is also possible to support the reaction product of metallocene compound and cocatalyst. Suitable support materials are, for example, silica gels, aluminum oxides, solid aluminoxane or other inorganic support materials such as magnesium chloride. Another suitable support material is a polyolefin powder in finely divided form. The preparation of the supported cocatalyst can be carried out, for example, as described in EP 567 952.

Preferably, the cocatalyst, e.g. aluminoxane, is applied to a support such as silica gels, aluminum oxides, solid aluminoxane, other inorganic support materials or a polyolefin powder in finely divided form and then reacted with the metallocene.

As inorganic supports, use can be made of oxides which have been produced flame-pyrolytically by combustion of element halides in a hydrogen/oxygen flame or can be prepared as silica gels in particular particle size distributions and particle shapes.

The preparation of the supported cocatalyst can be carried out, for example, as described in EP 578 838 in the following manner in a stainless steel reactor having an explosion proof design provided with a pumped circulation system having a pressure rating of 60 bar and provided with inert gas supply, temperature control by means of jacket cooling and a second cooling circuit via a heat exchanger on the pumped circulation system. The pumped circulation system draws in the contents of the reactor through a connection in the bottom of the reactor by means of a pump and pushes it into a mixer and through a riser line via a heat exchanger back into the reactor. The mixer is configured such that the inlet has a constricted tube cross section in which the flow velocity is increased and into whose turbulence zone there leads, axially and opposite to the flow direction, a thin feed line through which, pulsed, a defined amount of water under 40 bar of argon can be fed in. The reaction is controlled by means of a sampler on the pumped circuit.

However, other reactors are also suitable in principle.

The above-described reactor having a volume of 16 dm$^3$ is charged with 5 dm$^3$ of decane under inert conditions. 0.5 dm$^3$ (=5.2 mol) of trimethylaluminum are added at 25° C. 250 g of silica gel SD 3216-30 (Grace AG), which have previously been dried at 120° C. in an argon-fluidized bed are then introduced into the reactor through a solids funnel and are homogeneously distributed by means of the stirrer and the pumped circulation system. A total amount of 76.5 g of water is added to the reactor over a period of 3.25 hours in portions of 0.1 cm$^3$ every 15 seconds. The pressure, resulting from the argon and the gases evolved, is kept constant at 10 bar by means of a pressure regulation valve. After all the water has been introduced, the pumped circulation system is switched off and stirring is continued for a further 5 hours at 25° C.

The supported cocatalyst prepared in this way is used as a 10% strength suspension in n-decane. The aluminum content is 1.06 mmol of Al per cm$^3$ of suspension. The isolated solid containst 31% by weight of aluminum, and the suspension medium contains 0.1% by weight of aluminum.

Further possible ways of preparing a supported cocatalyst are described in EP 578 838.

The metallocene of the invention is then applied to the supported cocatalyst by stirring the dissolved metallocene with the supported cocatalyst. The solvent is removed and replaced by a hydrocarbon in which both cocatalyst and the metallocene are insoluble.

The reaction to produce the supported catalyst system is carried out at a temperature of from −20 to +120° C., preferably from 0 to 100° C., particularly preferably at from 15 to 40° C. The metallocene is reacted with the supported cocatalyst by combining the cocatalyst as a 1–40% strength by weight, preferably 5–20% strength by weight, suspension in an aliphatic, inert suspension medium such as n-decane, hexane, heptane or diesel oil with a solution of the metallocene in an inert solvent such as toluene, hexane, heptane or dichloromethane or with the finely milled solid metallocene. Conversely, a solution of the metallocene can also be reacted with the solid cocatalyst.

The reaction is carried out by intensive mixing, for example by stirring, at a molar Al/M$^1$ ratio of from 100/1 to 10,000/1, preferably from 100/1 to 3000/1, and a reaction time of from 5 to 120 minutes, preferably from 10 to 60 minutes, particularly preferably from 10 to 30 minutes, under inert conditions. During the course of the reaction for preparing the supported catalyst system, particularly when using the metallocenes of the invention having absorption maxima in the visible region, changes in the color of the reaction mixture occur and these can be used to follow the progress of the reaction.

After the reaction time has expired, the supernatant solution is separated off, for example by filtration or decantation. The remaining solid is washed from 1 to 5 times with an inert suspension medium such as toluene, n-decane, hexane, diesel oil or dichloromethane to remove soluble constituents in the catalyst formed, in particular to remove unreacted and therefore soluble metallocene.

The supported catalyst system prepared in this way can be resuspended as a vacuum-dried powder or while still moist with solvent and metered as a suspension in one of the abovementioned inert suspension media into the polymerization system.

If the polymerization is carried out as a suspension or solution polymerization, use is made of an inert solvent customary for the Ziegler low-pressure process. For example, the polymerization is carried out in an aliphatic or cycloaliphatic hydrocarbon, for example propane, butane, hexane, heptane, isooctane, cyclohexane or methylcyclohexane. It is also possible to use a petroleum or hydrogenated diesel oil fraction. Toluene can also be used. Preference is given to carrying out the polymerization in the liquid monomer.

The present invention is illustrated by the following examples.

EXAMPLES

Example 1

3.0 g (6.9 mmol) of rac-isopropylidenebis(indenyl)zirconium dichloride and 0.3 g (0.28 mmol) of palladium (10% on activated carbon) were suspended in 100 ml of toluene and hydrogenated at 50° C. under a hydrogen pressure of 60 bar. After 6 hours, the reaction mixture was filtered hot, extracted with 200 ml of hot toluene and evaporated to 40 ml. The product crystallized out at 0–5° C. Yield:1.9 g (4.3 mmol; 63%) of rac-isopropylidenebis(4,5,6,7-tetrahydroindenyl)zirconium dichloride. $^1$H-NMR (300 MHz, CDCl$_3$): d=6.37 (d, 2H); 5.48 (d, 2H); 2.6–3.0 (m, 6H); 2.3–2.5 (m, 2H); 1.4–2.0 (m, 8H); 1.85 (s, 6H).

Example 2

3.0 g (7.8 mmol) of isopropylidene(cyclopentadienyl)(indenyl)zirconium dichloride and 0.3 g (0.28 mmol) of palladium (10% on activated carbon) were suspended in 100 ml of toluene and hydrogenated at 50° C. under a hydrogen pressure of 20 bar. After 6 hours, the reaction mixture was filtered hot and evaporated to 40 ml. The product crystallized out at 0–5° C. Yield: 2.1 g (5.4 mmol; 69%) of isopropylidene(cyclopentadienyl)(4,5,6,7-tetrahydroindenyl)zirconium dichloride. $^1$H-NMR (300 MHz, CDCl$_3$): d=6.78 (m, 1H); 6.62 (m, 1H); 6.25 (m, 1H); 5.72 (m, 1H); 5.62 (m, 2H); 2.9–2.6 (m, 3H); 2.5–2.3 (m, 1H); 2.0–1.3 (m, 4H); 1.90 (s, 3H); 1.80 (s, 3H).

We claim:

1. A metallocene of the formula I

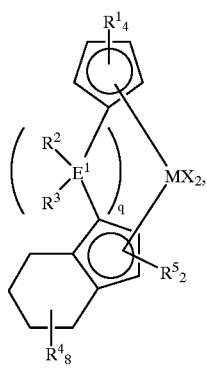

(I)

where

M is a metal of group IVb, Vb or VIb of the Periodic Table of the Elements,

X are identical or different and are each a hydrogen atom, a $C_1$–$C_{40}$-hydrocarbon group, $C_1$–$C_{10}$-alkoxy, $C_6$–$C_{10}$-aryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl group, an OH group, a halogen atom or a pseudohalogen, $R^1$ to $R^5$ are identical or different and, independently of one another, are each a hydrogen atom, a $C_1$–$C_{30}$-hydrocarbon radical or a carbon-containing radical having from 1 to 10 carbon atoms and one or more heteroatoms selected from the group consisting of O, N, Si, Ge and P, where in each case two adjacent radicals $R^4$ together with the carbon atoms connecting them can form a ring system, $E^1$ is a carbon atom, silicon, germanium or tin atom, and q is 0 or 1.

2. A metallocene of the formula I as claimed in claim 1, wherein

M is zirconium or hafnium,

X is a $C_1$–$C_4$-alkyl, $C_1$–$C_3$-alkoxy, $C_6$–$C_8$-aryl, $C_6$–$C_8$-aryloxy, $C_2$–$C_4$-alkenyl, $C_7$–$C_{12}$-arylalkyl, $C_7$–$C_{12}$-alkylaryl or $C_8$–$C_{12}$-arylalkenyl group or halogen, $R^2$ and $R^3$ are $C_1$–$C_4$-alkyl or $C_6$–$C_{14}$-aryl.

3. A metallocene as claimed in claim 1 said metallocene being isopropylidene(cyclopentadienyl)(4,5,6,7-tetrahydroindenyl)zirconium dichloride, diphenylmethylene(cyclopentadienyl)(4,5,6,7-tetrahydroindenyl)zirconium dichloride, methylphenylmethylene(cyclopentadienyl)(4,5,6,7- tetrahydroindenyl)zirconium dichloride, isopropylidene (cyclopentadienyl)(4,5,6,7- tetrahydroindenyl)hafnium dichloride, diphenylmethylene(cyclopentadienyl)(4,5,6,7-tetrahydroindenyl)hafnium dichloride, methylphenylmethylene(cyclopentadienyl)(4,5,6,7-tetrahydroindenyl)hafnium dichloride.

4. A metallocene of the formula I as claimed in claim 1, which has been prepared by the process comprising hydrogenation of a starting material corresponding to the compound of formula I except for the presence of at least one additional double bond or at least one, or at least one additional, fused six-member aromatic ring, or at least one additional double bond and at least one, or one additional, fused six-member aromatic ring, as compared to said starting material.

5. A metallocene of the formula I as claimed in claim 4, wherein said hydrogenation comprises the treatment of said starting material with hydrogen in a hydrogenation medium comprising a nonhalogenated solvent and in the presence of at least one hydrogenation catalyst.

6. A metallocene of the formula I as claimed in claim 1, wherein:

M is Ti, Zr, or Hf;

X is hydrogen; a halogen or a pseudohalogen, wherein said pseudohalogen is nitrile; a said alkoxy, a said aryl, a said aryloxy, a said alkenyl, a said arylakyl, a said alkylaryl, or a said arylakenyl group;

$R^1$ and $R^5$ are each hydrogen, a $C_1$–$C_{20}$-alkyl group, a $C_6$–$C_{20}$-aryl group, or a said carbon-containing radical; and $E^1$ is a carbon atom; and q is 1.

7. A metallocene of the formula I as claimed in claim 2, wherein q is 1.

8. A metallocene of the formula I as claimed in claim 1, wherein the $R^1$ radicals are identical or different and are hydrogen or a $C_1$–$C_{30}$-hydrocarbon group.

9. A catalyst composition which is the combination or product of the components comprising: a) at least one metallocene as claimed in claim 1 and b) at least one cocatalyst.

10. A catalyst as claimed in claim 9, wherein said catalyst is supported by a support material.

11. A catalyst as claimed in claim 10, wherein said catalyst is in prepolymerized form.

12. A catalyst as claimed in claim 9, wherein said catalyst is in prepolymerized form.

13. A process for preparing an olefin polymer comprising the step of polymerizing at least one olefin in the presence of a catalyst as claimed in claim 9.

14. The metallocene as claimed in claim 1, wherein

X are identical or different and are each a hydrogen atom, $C_1$–$C_{10}$-alkoxy, $C_6$–$C_{10}$-aryl, $C_6$–$C_{10}$-aryloxy, $C_2$–$C_{10}$-alkenyl, $C_7$–$C_{40}$-arylakyl, $C_7$–$C_{40}$-alkylaryl or $C_8$–$C_{40}$-arylalkenyl group, an OH group, a halogen atom or a pseudohalogen, $R^1$ to $R^5$ are identical or different and, independently of one another, are each a hydrogen atom, a $C_1$–$C_{20}$-alkyl or $C_6$–$C_{20}$-aryl, or a carbon-containing radical having from 1 to 10 carbon atoms and one or more heteroatoms selected from the group consisting of O, N, Si, Ge and P, where in each case two adjacent radicals $R^4$ together with the carbon atoms connecting them can form a ring system.

15. A metallocene of the formula I

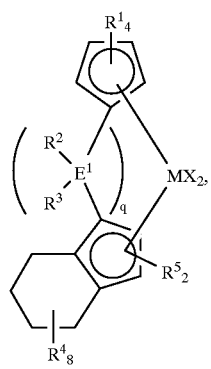

(I)

where

M is a metal of group IVb, Vb or VIb of the Periodic Table of the Elements,

X are identical or different and are each a hydrogen atom, a $C_1$–$C_{40}$-hydrocarbon group, $C_1$–$C_{10}$-alkoxy, $C_6$–$C_{10}$-aryl, $C_6$–$C_{10}$-aryloxy, $C_2$–$C_{10}$-arylalkenyl group, an OH group, a halogen atom or a pseudohalogen, $R^1$ to $R^5$ are identical or different and, independently of one another, are each a hydrogen atom, a $C_1$–$C_{30}$-hydrocarbon radical or a carbon-containing radical having from 1 to 10 carbon atoms and one or more heteroatoms selected from the group consisting of O, N, Si, Ge and P;

$E^1$ is a carbon, silicon, germanium or tin atom, and q is 0 or 1.

16. A metallocene of the formula I as claimed in claim 15, wherein

M is zirconium or hafnium,

X is a $C_1$–$C_4$-alkyl, $C_1$–$C_3$-alkoxy, $C_6$–$C_8$-aryl, $C_6$–$C_8$-aryloxy, $C_2$–$C_4$-alkenyl, $C_7$–$C_{12}$-arylalkyl, $C_7$–$C_{12}$-alkylaryl or $E^1$ is a carbon atom, $R^2$ and $R^3$ are $C_1$–$C_4$-alkyl or $C_6$–$C_{14}$-aryl and q is 1.

17. A metallocene of the formula I as claimed in claim 15, wherein q is 1.

18. A catalyst composition which the combination or product of the components comprising: a) at least one metallocene as claimed in claim 15 and b) at least one cocatalyst.

\* \* \* \* \*

UNITED STATES PATENT AND TRADEMARK OFFICE
CERTIFICATE OF CORRECTION

PATENT NO. : 6,153,549
DATED : November 28, 2000
INVENTOR(S) : Erich Hübscher et al.

It is certified that error appears in the above-identified patent and that said Letters Patent is hereby corrected as shown below:

Column 11,
Line 66, delete "$C_1$-$C_{10}$-alkoxy, $C_6$-$C_{10}$-aryl, $C_8$-$C_{10}$ -aryloxy, $C_2$-$C_{10}$-alkenyl, $C_7$-$C_{40}$ -arylalkyl, $C_7$-$C_{40}$-alkylaryl or $C_8$-$C_{40}$-arylalkenyl group,".

Column 12,
Line 57, "$E^1$ is a carbon atom; and" should have been deleted.

Column 14,
Line 7, after "aryloxy, $C_2$-$C_{10}$" the following should be inserted
-- -alkenyl, $C_7$-$C_{40}$-arylalkyl,$C_7$-$C_{40}$-alkylaryl or $C_8$-$C_{40}$- --
Line 25, after "alkylaryl or" -- $C_8$-$C_{12}$-arylalkenyl group or halogen -- should be inserted.

Signed and Sealed this

First Day of April, 2003

JAMES E. ROGAN
*Director of the United States Patent and Trademark Office*